United States Patent [19]

Miller

[11] 4,039,679
[45] Aug. 2, 1977

[54] TREATMENT OF INCREASED BODY TEMPERATURE WITH SUBSTITUTED HEXAHYDRO-1H-FURO(3,4-C)PYRROLE COMPOUNDS

[75] Inventor: Alfred D. Miller, Wilmington, Del.

[73] Assignee: ICI United States Inc., Wilmington, Del.

[21] Appl. No.: 665,302

[22] Filed: Mar. 9, 1976

Related U.S. Application Data

[60] Continuation-in-part of Ser. No. 566,418, April 9, 1975, Pat. No. 3,975,532, which is a division of Ser. No. 370,010, June 14, 1973, Pat. No. 3,910,950.

[51] Int. Cl.$^2$ .............................................. A61K 31/40
[52] U.S. Cl. ................................................... 424/274
[58] Field of Search ........................................ 424/274

Primary Examiner—Stanley J. Friedman

[57] ABSTRACT

Disclosed is a method of treating an animal exhibiting elevated body temperature or fever by administering to said animal an effective amount of a compound represented by the formula

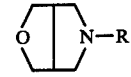

wherein R is a radical selected from the group consisting of phenyl; benzoyl; thenoyl; naphthoyl; phenylacetyl; mono-, di- or tri-halogen substituted benzoyl where the halogen substitution is on the phenyl ring; mono-, di- or tri-halogen substituted phenylacetyl where the halogen substitution is on the phenyl ring; phenylalkyl where the alkyl group contains from 1 to 4 carbon atoms; mono-, di- or tri-halogen substituted phenylalkyl where the alkyl group contains from 1 to 4 carbon atoms and the halogen is substituted on the phenyl ring and the pharmacologically acceptable acid addition salts thereof.

10 Claims, No Drawings

TREATMENT OF INCREASED BODY TEMPERATURE WITH SUBSTITUTED HEXAHYDRO-1H-FURO(3,4-C)PYRROLE COMPOUNDS

This application is a continuation-in-part of my copending application Ser. No. 566,418 filed Apr. 9, 1975, now U.S. Pat. No. 3,975,532 which in turn is a division of application Ser. No. 370,010 filed June 14, 1973, now U.S. Pat. 3,910,950.

The present invention relates to a method of treating animals, more particularly mammals, suffering from fever or elevated body temperature.

Certain substituted hexahydro-1H-furo(3,4-c)pyrrole compounds, the preparation of which is disclosed in U.S. Pat. No. 3,910,950, have been found to exhibit significant antipyretic activity in animals. It has been found that fever or elevated temperature in animals, more particularly in mammals, can be effectively treated by the administration of an effective amount of a compound represented by the formula

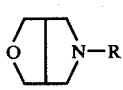

(a)

wherein R is phenyl; benzoyl; thenoyl; naphthoyl; phenylacetyl; mono-, di- or tri-halogen substituted benzoyl where the halogen substitution is on the phenyl ring; mono-, di- or tri-halogen substituted phenylacetyl where the halogen substitution is on the phenyl ring; phenylalkyl where the alkyl group contains from 1 to 4 carbon atoms; mono-, di- or tri-halogen substituted phenylalkyl where the alkyl group contains from 1 to 4 carbon atoms and the halogen is substituted on the phenyl ring and the pharmacologically acceptable acid addition salts thereof. When halogen is referred to in relation to any of the radicals represented by R in formula (a), fluorine, chlorine, iodine and bromine are included; however, fluorine, chlorine and bromine are preferred.

In a preferred subclass of the present invention, R in formula (a) above is benzoyl, thenoyl, naphthoyl, o-, m- or p-halophenethyl, phenylacetyl and o-, m- or p-halobenzoyl.

Amongst the substituted hexahydro-1H-furo(3,4-c)pyrrole compounds that can be used in the present method are: 5-benzoylhexahydro-1H-furo(3,4-c)pyrrole, 5-(p-chlorophenethyl)-hexahydro-1H-furo(3,4-c)pyrrole, 5-phenylacetyl-hexahydro-1H-furo(3,4-c)pyrrole, 5-(p-chlorobenzoyl)-hexahydro-1H-furo(3,4-c)pyrrole, 5-(o-chlorobenzoyl)-hexahydro-1H-furo(3,4-c)pyrrole, 5-(3,4-dichlorobenzoyl)-hexahydro-1H-furo(3,4-c)pyrrole, 5-phenethylhexahydro-1H-furo(3,4-c)pyrrole, 5-thenoyl-hexahydro-1H-furo(3,4-c)pyrrole, 5-naphthoyl-hexahydro-1H-furo(3,4-c)pyrrole, 5-phenyl-hexahydro-1H-furo(3,4-c)pyrrole, 5-(3,4-dichlorophenylacetyl)-hexahydro-1H-furo(3,4-c)pyrrole, 5-phenylpropylhexahydro-1H-furo(3,4-c)pyrrole, 5-(3,4-dichlorophenylbutyl)-1H-furo(3,4-c)pyrrole, 5-(3,4-difluorobenzoyl)-hexahydro-1H-furo(3,4-c)pyrrole and 5-(m-bromobenzoyl)-1H-furo(3,4-c)pyrrole.

Evaluation in laboratory animals indicates that the present compounds possess antipyretic activity when administered in a therapeutically effective amount. The effectiveness and dosage required vary as is customary in this art with the species being treated, particular disorder being treated, weight of the animal and the route of administration. In accordance with the present invention, the subject compounds are administered in doses from about 0.5 mg. to 400 mg. per kilogram body weight 1 to 4 times a day. A more preferred dose is from about 1.0 mg. to 300 mg. per kilogram body weight 1 to 4 times a day.

The antipyretic activity obtained by the method of the present invention is illustrated in the following examples through the use of yeast induced pyresis.

EXAMPLE 1

Male albino Wistar rats (160–180 grams) were made hyperthermic by subcutaneous administration of a solution of 20% (weight/volume) Brewer's yeast in saline solution at the dosage level of 5 ml. per kilogram body weight. Eighteen hours later the rats were given the test drugs listed in Table I or a saline placebo via oral intubation and the rectal temperatures of the animals tested were recorded at 60 and 120 minutes post-drug administration. Individual drug groups were compared to the placebo control by Student's t-test and ED50 values for antipyretic activity were calculated by the method of Litchfield and Wilcoxon, J. Pharmacol. Exp. Therap. 96, 99–113 (1949). The results obtained are summarized in the following table.

TABLE I

| | Drug | $N^1$ | ED50 $(mg/kg, p.o.)^2$ | 95% Fiducial Limits$^2$ |
|---|---|---|---|---|
| (a) | 5-Benzoyl-Hexahydro-1H-Furo(3,4-c)Pyrrole | 36 | 58.0 | 38.7 – 87.0 |
| (b) | Aspirin | 36 | 54.0 | 46.1 – 63.2 |
| (c) | Acetaminophen | 36 | 28.5 | 24.0 – 33.8 |
| (d) | d-Propoxyphene HCl | 48 | Inactive $(65)^3$ | — |

$^1$Number of rats used.
$^2$ED50 and 95% fiducial limits were calculated by the method of Litchfield and Wilcoxon, J. Pharmacol. Exp. Therap. 96 99-113 (1949).
$^3$Highest dose tested.

EXAMPLE 2

Six rats were each injected with 5 ml. per kilogram body weight of a solution of 20% (weight/volume) Brewer's yeast in saline and, then 18 hours later, the same animals were injected with the drugs at the dosage levels indicated in the following Table II. Six other rats for each dosage level were also injected with a 20% solution (weight/volume) Brewer's yeast in saline and, then 18 hours later, the same animals were injected with saline solution. The mean temperature change (Δ)° C. referred to in the following Table II represents the decrease in body temperature of the six animals at the particular drug dosage level as compared to the controls injected with the Brewer's yeast solution and saline.

The control in the following Table represents a combined saline control from several days studies wherein 114 rats were first treated with a solution of 20% Brewer's yeast (weight/volume) in saline and, then 18 hours later, these same animals were treated with just saline solution.

TABLE II
Effect On Elevated Temperature

| | Dose (mg/kg) P.O. | 1 Hour Post Injection Mean Temp.Δ °C. | 2 Hours Post Injection Mean Temp.Δ °C. |
|---|---|---|---|
| 0.9% Saline Control | 5 ml/kg | 0.22±0.10 | 0.14±0.07 |
| 5-Benzoyl-Hexahydro-1H-Furo(3,4-c)Pyrrole | 10 | −0.73 | −0.87 |
| | 30 | −1.82 | −1.78 |
| | 100 | −2.30 | −1.84 |
| 5-(p-Chlorophenethyl)-Hexahydro-1H-Furo(3,4-c)Pyrrole | 200 | −0.97 | −0.73 |
| Aspirin | 50 | 0.18 | 0.52 |
| | 150 | −1.10 | −1.47 |

As the compounds coming within the scope of the present invention are effective upon oral administration, they can be compounded into any suitable oral dosage form, such as in tablet, syrup, elixir, suspension or other solid or liquid forms which can be prepared by procedures well known in the pharmaceutical art. Thus the compounds used in the present method can be mixed with a suitable diluent such as lactose or kaolin and encapsulated or they can be combined with suitable binding agents and expanding agents and pressed into tablets. In addition, a liquid pharmaceutical may be obtained by dissolving, dispersing or suspending the compounds of the present method with a suitable flavored liquid. The present compounds are also considered active upon parenteral and rectal administration.

Examples of formulations for preparing tablets, capsules, liquids, parenterals and suppositories containing the novel compounds of the present invention are described below. Obviously it will be recognized by one skilled in the present art that the following formulations represent only one method of preparing such pharmaceutical compositions and obviously the size of the tablet or capsule or the strength of the dosage form may be suitably varied in order to satisfy the particular requirements such as dosage level indicated. For example each dosage unit may conventionally contain from 15 mg. to 5000 mg. of the active ingredient admixed with a diluent amount of a pharmaceutically acceptable carrier. Any of the well-known pharmaceutical carriers can be used to prepare acceptable dosage forms so as to provide an effective amount or a therapeutically effective amount of the compound to be administered.

| Tablet Containing 100 mg. of 5-Phenylacetyl-Hexahydro-1H-Furo(3,4-c)Pyrrole | 1000 Tablets (Grams) |
|---|---|
| 5-Phenylacetyl-Hexahydro-1H-Furo(3,4-c)Pyrrole | 100 |
| Starch | 80 |
| Powdered Lactose | 80 |
| Talc | 20 |
| Weight of Granulation | 280 |

Combine all ingredients, mix, and then compress into slugs. The slugs should then be ground to form granules that will pass through a 14 to 16 mesh screen. The granules may then be recompressed into tablets using a suitable compression mold to form tablets, each weighing 280 mg.

| Capsule Containing 200 mg. of 5-(m-Chlorophenylacetyl)Hexahydro-1H-furo(3,4-c)pyrrole | |
|---|---|
| 5-(m-Chlorophenylacetyl)Hexahydro-1H-furo(3,4c)pyrrole | 200 mg |
| Powdered Lactose | 100 mg |
| D.T.D. Capsules No. 1000 | |

Mix the ingredients so as to evenly distribute the active ingredient throughout the lactose. Pack the powder into a No. 1 empty gelatin capsule.

| Suspension Containing 50 mg per 5 cc of 5-Benzoyl-Hexahydro-1H-Furo(3,4-c)Pyrrole | |
|---|---|
| 5-Benzoyl-Hexahydro-1H-Furo(3,4-c)pyrrole | 10 grams |
| Tragacanth | 50 grams |
| Amaranth | 10 grams |
| Syrup Wild Cherry | 60 ml |
| Distilled Water q.s. | 1000 ml |

Hydrate the tragacanth with sufficient water to form a smooth paste and to this add the 5-benzoyl-hexahydro-1-H-furo (3,4-c)pyrrole, followed by the amaranth which has been previously dissolved in water. Then add the syrup of wild cherry and add distilled water to make 1000 ml.

| Injectable Containing 5 mg of 5-Phenethyl-Hexahydro-1H-Furo(3,4-c)Pyrrole Hydrochloride Per Milliliter Suitable for Intramuscular, Intraperitoneal or Subcutaneous Injection | |
|---|---|
| 5-Phenethyl-Hexahydro-1H-Furo(3,4-c)Pyrrole Hydrochloride | 5.0 grams |
| Chlorobutanol | 3.0 grams |
| Propylene Glycol | 20.0 ml |
| Water for Injection q.s. | 1000.0 ml |

Combine the above ingredients, clarify by filtration, fill into vials, seal, and autoclave.

What is claimed is:

1. A method for the treatment of an animal suffering from an elevated body temperature comprising administering to said animal a therapeutically effective amount for antipyritic effect of a compound of the formula

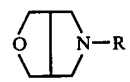

wherein R is phenyl; benzoyl; thenoyl; naphthoyl; phenylacetyl; mono-, di- or tri-halogen substituted benzoyl where the halogen substitution is on the phenyl ring; mono-, di- or tri-halogen substituted phenylacetyl where the halogen substitution is on the phenyl ring; phenylalkyl where the alkyl group contains from 1 to 4 carbon atoms; mono-, di- or tri-halogen substituted phenylalkyl where the alkyl group contains from 1 to 4 carbon atoms and the halogen is substituted on the phenyl ring and the pharmacologically acceptable acid addition salt thereof.

2. A method of claim 1 wherein 5-benzoylhexahydro-1H-furo(3,4-c)pyrrole is administered.

3. A method of claim 1 wherein 5-(p-chlorophenethyl)-hexahydro-1H-furo(3,4-c)pyrrole is administered.

4. A method of claim 2 wherein from about 0.5 mg. to 400 mg. per kilogram body weight of 5-benzoylhexahydro-1H-furo(3,4-c)pyrrole is administered.

5. A method of claim 3 wherein from about 0.5 mg. to 400 mg. per kilogram body weight of 5-(p-chlorophenethyl)-hexahydro-1H-furo(3,4-c)pyrrole is administered.

6. A method of claim 3 wherein a pharmacologically acceptable acid addition salt of 5-(p-chlorophenethyl)-hexahydro-1H-furo(3,4-c)pyrrole is administered.

7. A method of claim 5 wherein the hydrochloride salt is administered.

8. A method of claim 1 wherein 5-phenylacetylhexahydro-1H-furo(3,4-c)pyrrole is administered.

9. A method of claim 1 wherein 5-(o-chlorobenzoyl)-hexahydro-1H-furo(3,4-c)pyrrole is administered.

10. A method of claim 1 wherein 5-(p-chlorobenzoyl)hexahydro-1H-furo(3,4-c)pyrrole is administered.

* * * * *